(12) United States Patent
Hodgkins (10) Patent No.: US 11,109,900 B2
(45) Date of Patent: Sep. 7, 2021

(54) EXTRAMEDULLARY COMPRESSION AND FIXATION DEVICE, SYSTEM AND METHOD

(71) Applicant: GBR99 IP, LLC, Belleair, FL (US)

(72) Inventor: Chris W. Hodgkins, Miami, FL (US)

(73) Assignee: GBR99 IP, LLC, Belleair, FL (US)

( * ) Notice: Subject to any disclaimer, the term of this patent is extended or adjusted under 35 U.S.C. 154(b) by 165 days.

(21) Appl. No.: 16/204,650

(22) Filed: Nov. 29, 2018

(65) Prior Publication Data

US 2020/0170691 A1    Jun. 4, 2020

(51) Int. Cl.
*A61B 17/80* (2006.01)
*A61B 17/68* (2006.01)
*A61B 17/56* (2006.01)

(52) U.S. Cl.
CPC ........ *A61B 17/8004* (2013.01); *A61B 17/809* (2013.01); *A61B 17/8085* (2013.01); *A61B 2017/564* (2013.01); *A61B 2017/681* (2013.01)

(58) Field of Classification Search
CPC .......... A61B 17/0642; A61B 2017/681; A61B 17/8004; A61B 17/808; A61B 17/8085; A61B 17/809; A61B 17/82; A61B 17/88; A61B 17/8872; A61B 2017/564
See application file for complete search history.

(56) References Cited

U.S. PATENT DOCUMENTS

| | | |
|---|---|---|
| 1,355,431 A | 10/1920 | Smart |
| 3,036,572 A | 5/1962 | Castelli et al. |
| 3,939,828 A | 2/1976 | Mohr et al. |
| 4,263,904 A * | 4/1981 | Judet ............ A61B 17/68 606/281 |
| 4,364,382 A * | 12/1982 | Mennen ......... A61B 17/8085 606/283 |
| 4,444,181 A | 4/1984 | Wevers et al. |
| 4,456,006 A | 6/1984 | Wevers et al. |
| 4,966,599 A * | 10/1990 | Pollock ......... A61B 17/1735 206/457 |
| 5,246,443 A | 9/1993 | Mai |
| 5,785,713 A | 7/1998 | Jobe |
| 6,287,307 B1 | 9/2001 | Abboudi |
| 6,315,780 B1 | 11/2001 | Lalonde |
| 6,620,165 B2 | 9/2003 | Wellisz |

(Continued)

FOREIGN PATENT DOCUMENTS

| | | |
|---|---|---|
| CH | 373516 | 1/1964 |
| EP | 0867149 B1 | 9/2000 |

(Continued)

*Primary Examiner* — Samuel S Hanna
(74) *Attorney, Agent, or Firm* — Gordon & Jacobson, P.C.

(57) ABSTRACT

An extramedullary compression and fixation apparatus consists of a pre-curved, malleable band having a first end and a second end, and at least one bone engaging structure protruding from the band toward an interior space defined by the band. The band is configured to be compressed (e.g., crimped) over a bone fracture site to conform the curvature of the band to a curvature of a surface of bone around the bone fracture site. The at least one bone engaging structure is configured to dig into the outer cortex of the bone when the band is compressed. The band is configured to maintain compression of the bone across the bone fracture upon the band being compressed without additional external fixation devices.

16 Claims, 10 Drawing Sheets

(56) References Cited

U.S. PATENT DOCUMENTS

| | | |
|---|---|---|
| 7,052,499 B2 | 5/2006 | Steger et al. |
| 7,648,508 B2 * | 1/2010 | Lutz ................... A61B 17/02 |
| | | 606/86 R |
| 7,857,839 B2 | 12/2010 | Duong et al. |
| 7,867,265 B2 | 1/2011 | Beutter |
| 8,685,067 B2 | 4/2014 | King et al. |
| 8,728,082 B2 | 5/2014 | Fritzinger et al. |
| 9,089,378 B2 | 7/2015 | Riemer et al. |
| 9,101,399 B2 | 8/2015 | Kartalian et al. |
| 9,101,421 B2 * | 8/2015 | Blacklidge ......... A61B 17/8004 |
| 9,414,865 B2 | 8/2016 | Duggal et al. |
| 9,675,400 B2 | 6/2017 | Katrana et al. |
| 10,016,198 B2 * | 7/2018 | Morgan ............ A61B 17/0682 |
| 2003/0009192 A1 | 1/2003 | Emidio |
| 2004/0087955 A1 * | 5/2004 | Bordi ................ A61B 17/8085 |
| | | 606/74 |
| 2008/0027471 A1 | 1/2008 | Hauri |
| 2009/0036930 A1 | 2/2009 | Allison |
| 2011/0160730 A1 * | 6/2011 | Schonhardt .......... A61B 17/085 |
| | | 606/71 |
| 2012/0290017 A1 | 11/2012 | Haidukewych |
| 2013/0261674 A1 | 10/2013 | Fritzinger |
| 2014/0309639 A1 | 10/2014 | Averous et al. |
| 2015/0209093 A1 | 7/2015 | Dallis |
| 2015/0335367 A1 * | 11/2015 | Austin ..................... A61F 2/28 |
| | | 606/87 |
| 2016/0008041 A1 | 1/2016 | Makhlouf |
| 2016/0192970 A1 * | 7/2016 | Dayton ................ A61B 17/80 |
| | | 606/281 |

FOREIGN PATENT DOCUMENTS

| | | |
|---|---|---|
| SU | 1049054 A1 | 10/1983 |
| WO | WO2015131106 A1 | 9/2015 |

* cited by examiner

EXTRAMEDULLARY COMPRESSION AND FIXATION DEVICE, SYSTEM AND METHOD

BACKGROUND

1. Field

The disclosure relates to bone fixation apparatuses, systems, and methods.

2. State of the Art

Figure 1:
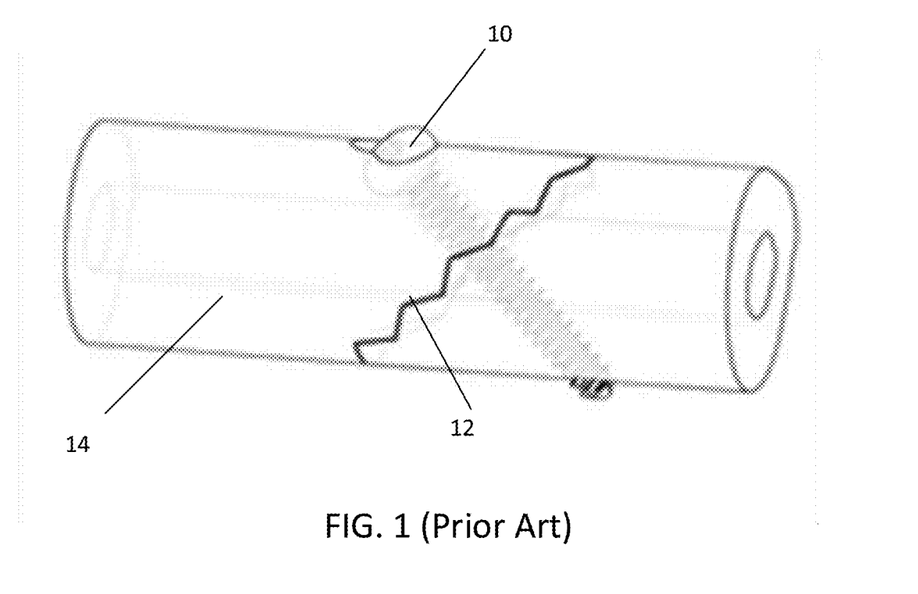
FIG. 1 shows a prior art lag screw placed orthogonal to a fracture plane in a bone, compressing and reducing the fracture.

When surgically repairing a bone fracture, it is frequently desirable to use a "lag screw" to compress the fragments together. The screw compresses the reduced fracture, which encourages primary bone healing and provides stability to the fracture which also promotes healing. FIG. 1 shows an example of a conventional lag screw 10 placement orthogonal to a fracture plane 12, compressing and reducing the fracture of the bone 14. The lag screw 10 alone is usually not enough to provide stability to the fracture. Thus, a traditional plate-and-screw construct is normally spanned across the bone fragments to provide additional fixation and stability.

For certain fractures, it is preferable to introduce an intramedullary nail or rod through the intramedullary canal of the bone. Screws through the bone and connected at each end of the rod may also be used to keep the fracture from shortening and/or rotating, and to hold the rod in place in the canal while the fracture is healing. The intramedullary rod and screws may be left in the bone after healing is complete.

The use of an intramedullary rod alone does not consistently reduce the fracture smoothly and evenly and does not compress the fracture. Importantly, the use of an intramedullary rod prevents the use of lag screws by obstructing the path (orthogonally through the fracture plane crossing the intramedullary canal) the screw would typically take.

SUMMARY

An extramedullary compression and fixation apparatus in accordance with an aspect of the disclosure provides a shapeable (malleable/conformal) compression and fixation "device" that applies a compressive clamping force orthogonal to the fracture plane. The extramedullary compression and fixation device is applied externally to the outer peripheral surface of the bone and does not pass through the fracture plane or the intramedullary canal on the inside of the bone. Thus, the extramedullary compression and fixation device can desirably compress and fixate the bone fragments without requiring the placement of a lag screw, or an intramedullary compression rod.

According to one aspect, further details of which are described herein, an extramedullary compression and fixation apparatus consists of a pre-curved, malleable band having a first end and a second end, and at least one bone engaging structure protruding from the band toward an interior space defined by the band. The band is configured to be compressed (e.g., crimped) over a bone fracture site and wrap at least 180 degrees about the peripheral surface of the bone. Upon the band being compressed, the band is configured to maintain compression on the bone across the bone fracture plane without requiring the application of any externally applied fixation devices around the band. Thus, no additional external compression is needed to maintain the band on the bone or to maintain the compressive force applied to the bone by the band. The at least one bone engaging structure can be any of a tooth, a pin, a ridge, a blade, or other cortically superficially engaging structure that is configured to dig into the outer cortex of the bone when the band is compressed to secure the band in position on the bone and inhibit relative movement therebetween.

In embodiments, the pre-curved, malleable band extends in a semicircle and the first and second ends are diametrically opposed to one another. Also, in embodiments, the curved malleable band extends along a portion of a helix, wherein the first and second ends are circumferentially spaced by 180 degrees about a central longitudinal axis of the helix.

The compression and fixation apparatuses described herein can be provided in different sizes for different sizes of bones (e.g., adult tibia vs. child tibia; tibia vs. radius). Also, the compression and fixation apparatuses described herein can be provided in different shapes for different shapes of bones. For example, the cross-sectional shape of a bone may vary along its length. The compression and fixation apparatuses may be provided having different malleability and/or thicknesses. Multiple different compression and fixation devices may be provided in a kit for a user.

In embodiments, at least one bone engaging structure is located at or near the first end of the band and at least one bone engaging structure is located at or near the second end of the band. Also, in embodiments, the first end and the second end of the band are configured for receiving retention features of an applier tool.

The applier tool is configured to retain the compression and fixation apparatus and hold it so that a user can position the compression and fixation apparatus against the bone while keeping a user's hands spaced from the bone. The applier tool permits the user, for example, to manipulate the compression and fixation apparatus in spaces between tissue and the bone so that the compression and fixation apparatus can be accurately positioned over the fracture and then compressed onto the bone.

The applier tool may have two pivoting lever arms joined and crossing at a fulcrum for scissor- or pliers-like movement. Proximal ends of the lever arms are configured as handles, and distal ends of the lever arm are configured as opposing jaws of a clamp. Squeezing the handles towards one another rotates the jaws towards one another in a clamping motion. Each jaw may have a tapered profile to facilitate positioning the jaws and the compression and fixation apparatus between tissue and bone. Each jaw may have one or more pin, tooth, ridge, blade, or other retention feature to engage with a corresponding or mating retention feature of the band of the compression and fixation apparatus in order to retain the compression and fixation apparatus to the applier tool while the user manipulates the applier tool and positions the compression and fixation apparatus onto the bone. The retention features can be disengaged after the user uses the applier tool to compress the compression and fixation apparatus onto the bone.

According to yet another aspect of the disclosure, the extramedullary compression and fixation apparatuses and applier tools described herein may comprise a fracture reduction system.

According to another aspect of the disclosure, a plurality of trial compression and fixation apparatuses is provided. Each trial compression and fixation apparatus is a model of a corresponding implantable extramedullary compression and fixation apparatus. The trial compression and fixation apparatuses are configured to facilitate determining which one of the plurality of trial compression and fixation apparatuses best fits a curvature of a fractured bone across a fracture plane of the fractured bone.

The trial compression and fixation apparatuses can be elastic, disposable, formed with or without bone engaging structures, and/or have different malleability than the corresponding implantable implant. Also, the trial compression and fixation apparatuses do not require an applier tool, though a handle may be provided to position the trial compression and fixation apparatuses against the bone to check the size and shape of the trial compression and fixation apparatus against the fractured bone. The handle may be integrally formed with the trials or may be interchangeable between the plurality of trial compression and fixation apparatuses.

According to another aspect of the disclosure, a fracture reduction kit includes at least one of a plurality of extramedullary compression and fixation apparatuses, a plurality of trial compression and fixation apparatuses, and an applier tool. Where the applier tool and at least one extramedullary compression and fixation apparatus are provided together in a kit, the applier tool may be pre-attached to the compression and fixation apparatus to permit the compression and fixation apparatus to be positioned over the bone. In accordance with another aspect, the kit may also include a plurality of different size and/or shape trial compression and fixation apparatuses.

According to yet another aspect of the disclosure, a method of bone fracture reduction includes applying one or more trial compression and fixation apparatus to a fractured bone across a fracture plane to determine which one trial compression and fixation apparatus is a best fit for the fractured bone across the fracture plane, selecting an implantable extramedullary compression and fixation apparatus corresponding to the trial compression and fixation apparatus determined to be the best fit, and crimping the selected implantable extramedullary compression and fixation apparatus to malleably deform the apparatus onto the bone over and across the fracture plane.

In embodiments, the selected implantable extramedullary compression and fixation apparatus is any of the extramedullary compression and fixation apparatuses described herein. In embodiments, the compression of the extramedullary compression and fixation apparatus causes the at least one bone engaging structure of the compression and fixation apparatus to dig into the cortex of the bone to inhibit relative movement between the bone and the compression and fixation apparatus.

DETAILED DESCRIPTION OF THE PREFERRED EMBODIMENTS

Figure 2:
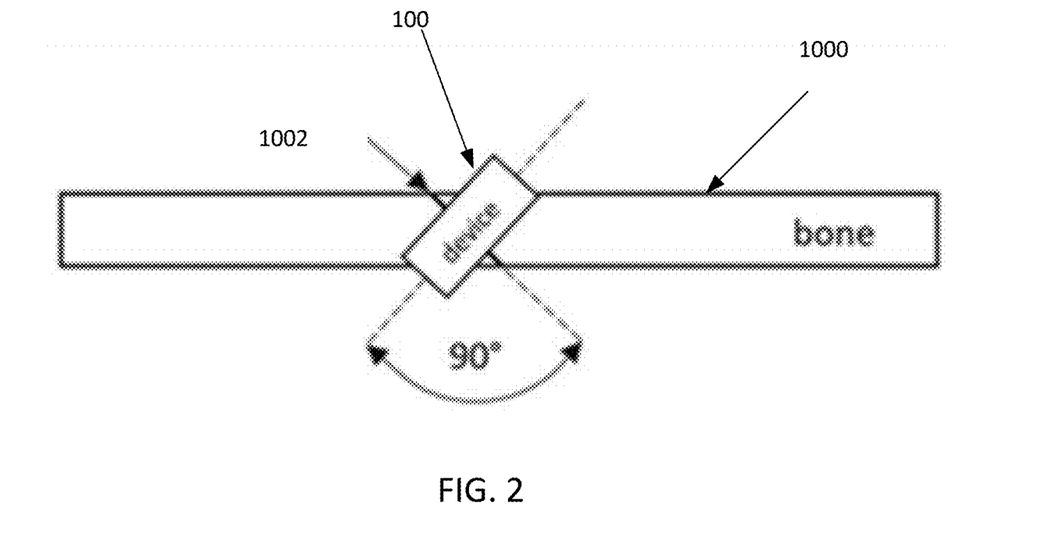
FIG. 2 is a schematic showing a fractured bone with a device in accordance with an aspect of the disclosure attached to the bone across the fracture plane.

FIG. 2 is a schematic showing a fractured bone 1000 partially banded by a compression and fixation device 100 configured in accordance with an aspect of the disclosure. The compression and fixation device 100 is attached to a bone 1000 across a fracture plane 1002. The compression and fixation device 100 is attached to the outside of the bone 1000 and straddles the fracture plane 1002 so that the device 100 applies compression to the bone 1000 from both sides of the fracture plane 1002. The compression and fixation device 100 is a shapeable (i.e., malleable/conformal) element that can externally apply compressive clamping force orthogonal to the fracture plane 1002. As used herein, malleable means capable of being extended or shaped by pressure. As will be noted in greater detail herein, the compression and fixation device 100 does not wrap completely (i.e., 360 degrees) around the bone 1000, which can allow for a cortical bone plate (e.g., 340, FIG. 3D; and 440, FIG. 4C) or other external (with respect to the outer surface(s) of the bone) device(s) to be attached to the bone 1000 in addition to the compression and fixation device 100.

Figure 3A:
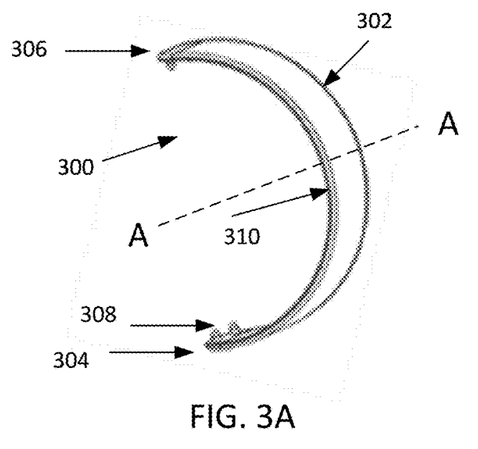
FIGS. 3A and 3B show an embodiment of a compression and fixation device, in an uncompressed state, in accordance with an aspect of the disclosure.
Figure 3B:
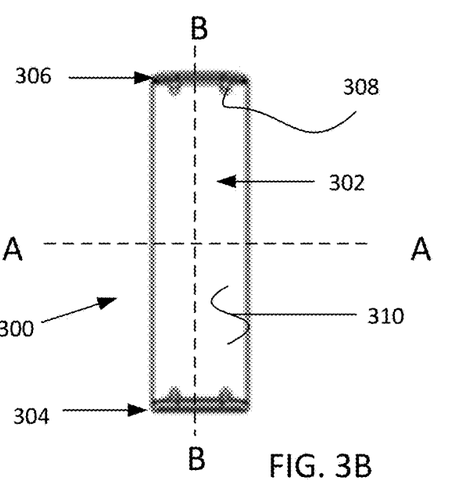
Figure 3C:
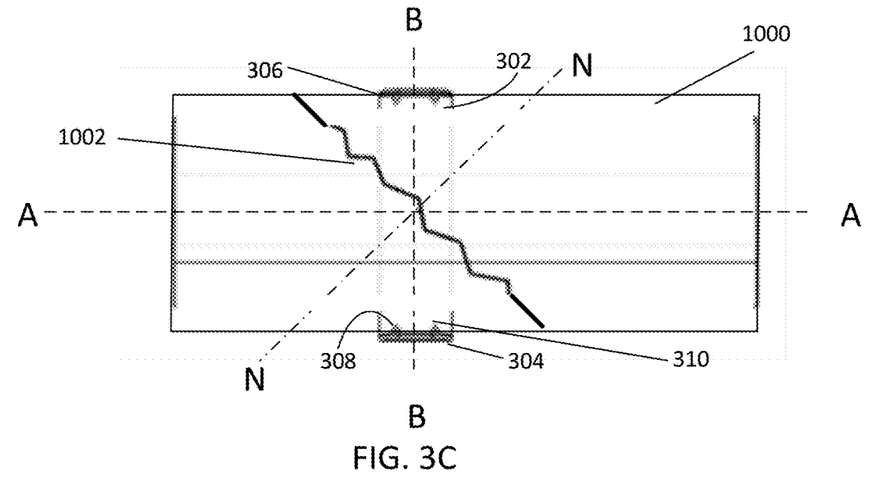
FIG. 3C shows the compression and fixation device of FIGS. 3A and 3B in a compressed state attached to a bone.

One embodiment of a compression and fixation device 300 is shown in FIGS. 3A to 3C. In FIGS. 3A and 3B the compression and fixation device is in an uncompressed state and is not secured to the bone 1000. In FIG. 3C, the compression and fixation device 300 is compressed and secured to the bone 1000. The device 300 is configured to be brought into contact with the bone and compressed onto the bone 1000 manually or by using an applier tool, such as the tool 920 shown in FIG. 9B, further details of which are described herein below.

The device 300 includes a relatively thin band 302 of malleable material that extends from a first end 304 to a second end 306. In embodiments, the band 302 is formed of biocompatible materials, including biocompatible metals (e.g., stainless steel) and/or plastics that are capable of being compressed over a bone and conform to the bone and remain conformal to the bone without the use or application of any banding or cerclage elements wrapped around the bone 1000 and the band 302 or additive fasteners coupling the band 302 to the bone 1000. That is, the band 302 inherently has sufficient material strength to be compressed onto a bone and, once bent, the band 302 has sufficient hoop strength to maintain compression on the bone without additional externally applied fasteners or banding elements around the band 302.

Figure 8A:
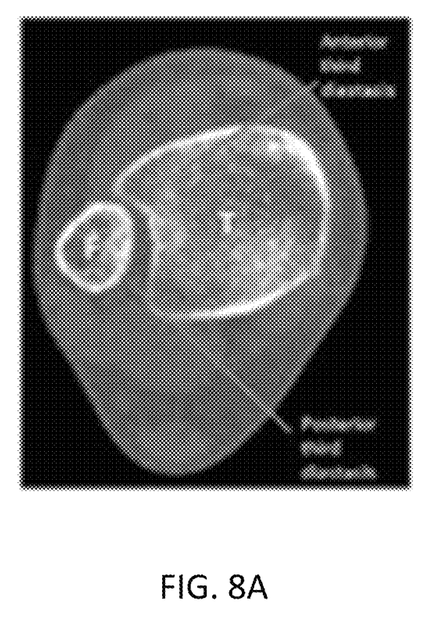
FIG. 8A shows a cross section of a portion of a human tibia and fibula at a first longitudinal position along the human leg.
Figure 8B:
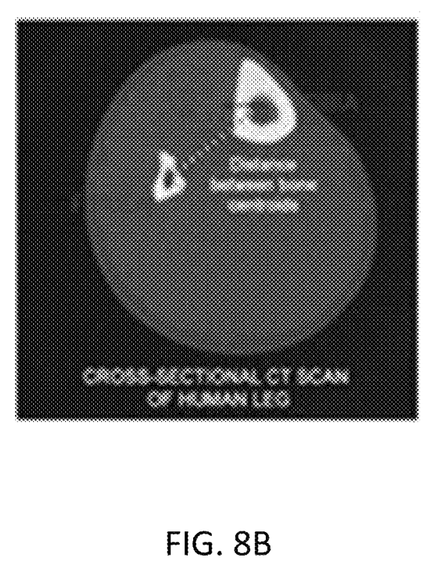
FIG. 8B shows a cross section of a portion of a human tibia and fibula at a second longitudinal position along the human leg.

The device 300 is pre-curved or otherwise pre-bent into certain shape. In its uncompressed state shown in FIGS. 3A and 3B, the device 300 is semi-circular and extends at least 180 degrees about a portion of a circle having a central axis A-A. The device 300 may be provided in various sizes and shapes to accommodate variation the sizes and shapes of bones. For example, even along the length of the same bone, such as that tibia and fibula in FIGS. 8A and 8B, the size and cross section of the bones can vary. Also, the device 300 may be provided with various malleability depending on the intended bone to which the device 300 will be attached.

Figure 7:
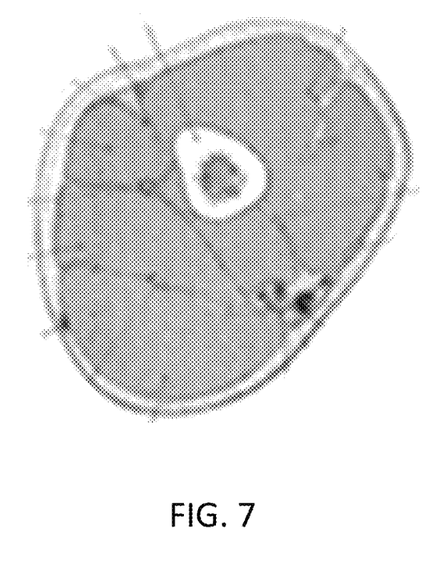
FIG. 7 shows a cross section of a portion of a humerus.

The pre-curved cross-sectional shape of the compression and fixation device 300 may have a non-circular shape intended to more closely match the cross sectional shape of the bone at the point of fixation. For example, compression and fixation devices 300 may be provided for specific bones, such as the humerus (e.g., FIG. 7) or the tibia and fibula (e.g., FIGS. 8A, 8B) and have a cross sectional shape in the undeformed configuration that more closely approximates the specific bone.

In order to ensure that a majority of the inner surface 310 of the compression and fixation device 300 makes contact with the outer periphery of the fractured bone 1000 it is connected to, the band 302 of the compression and fixation device 300 is sufficiently long enough to straddle the fracture plane 1002 and be compressed against the bone 1000 to conform to its peripheral surface. More specifically, the band 302 is sufficiently long so that when compressed onto the bone, the ends 304, 306 of the band will be at least 180 degrees apart from one another around the bone 1000. This permits application of opposing forces 180 degrees apart to compress and support reduction of the fracture.

As shown in FIG. 3B, in the undeformed (i.e., uncompressed) configuration of the device 300, the ends 304 and 306 of the device 300 are diametrically opposed from one another and align along axis B-B. In FIG. 3C, when the device 300 is compressed onto the bone 1000, the band 302 straddles the fracture plane 1002 so that the device 300 applies radial compression to the fractured bone 1000. Axis N-N is shown orthogonal to the fracture plane 1002. At least a portion of the radial compressive force applied by the device 300 resolves along axis N-N.

The device 300 also includes bone engagement structures 308 that are configured to anchor or otherwise securely engage the outer cortex of the fractured bone. Some examples of bone engagement structures include, a tooth, a pin, a ridge, a blade, or any other cortically superficially engaging structure. In the embodiment shown in FIGS. 3A to 3C, bone engagement structures 308 are located at or near the ends 304 and 306. The bone engagement structures 308 protrude from the band toward an interior space defined by the band 302. Specifically, in the example embodiment shown in FIGS. 3A to 3C, the bone engagement structures 308 protrude orthogonally from an inner surface 310 of the band 302. The bone engagement structures 308 are sharp enough that they can pierce the outer cortex of the bone 1000 when the device 300 is compressed onto the bone 1000.

Figure 4A:
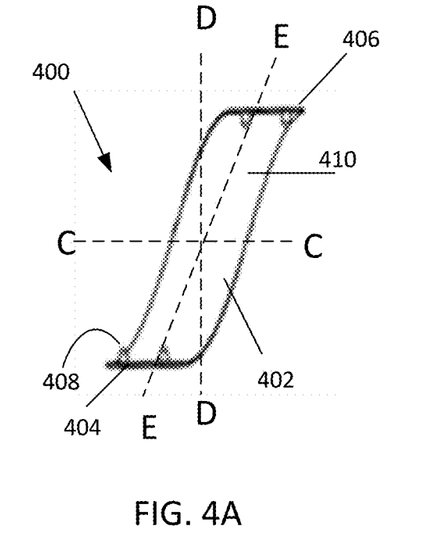
FIG. 4A show another embodiment of a compression and fixation device, in an uncompressed state.
Figure 4B:
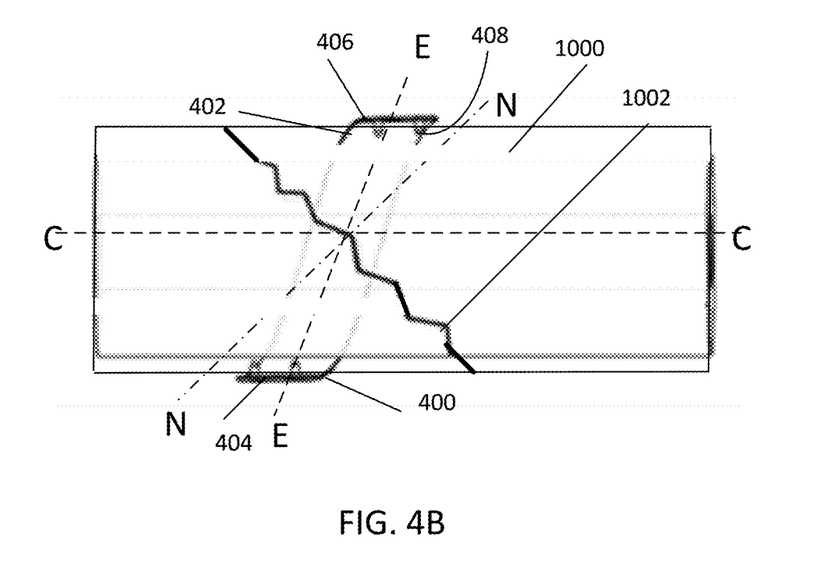
FIG. 4B shows the compression and fixation device of FIG. 4A in a compressed state attached to a bone.

FIGS. 4A and 4B show another embodiment of a compression and fixation device 400 that includes a helical band 402 that extends from a first end 404 to a second end 406. The device 400 includes bone engagement structures 408 at or near the ends 404 and 406 that protrude from the band 402 toward an interior space defined by the band 402. Specifically, the bone engagement structures 408 protrude orthogonally from an inner surface 410 of the band 402. In the undeformed configuration of the device 400 shown in FIG. 4B, the band 402 has a helical shape that extends partially about a central axis C-C. In some embodiments, the band 402 extends circumferentially around axis C-C by at least 180 degrees. The ends 404 and 406 are laterally offset from one another along axis C-C, so that when the device 400 is secured to the bone as in FIG. 4A, the band 402 crosses the fracture plane 1002 more orthogonally than the non-helical device 300. Thus, the compressive force applied by the device 400 is directionally applied more orthogonally with respect to the fracture plane 1002 than the device 300. For example, the angle between axis E-E and orthogonal axis N-N in FIG. 4B is much smaller than the angle between axis B-B and axis N-N in FIG. 3C. Thus, a greater amount of the compressive force applied by the helical implant 400 resolves along the orthogonal axis N-N in FIG. 4B, in comparison to the amount of compressive force applied by the non-helical implant 300 that resolves along the orthogonal axis N-N in FIG. 3C.

Figure 3D:
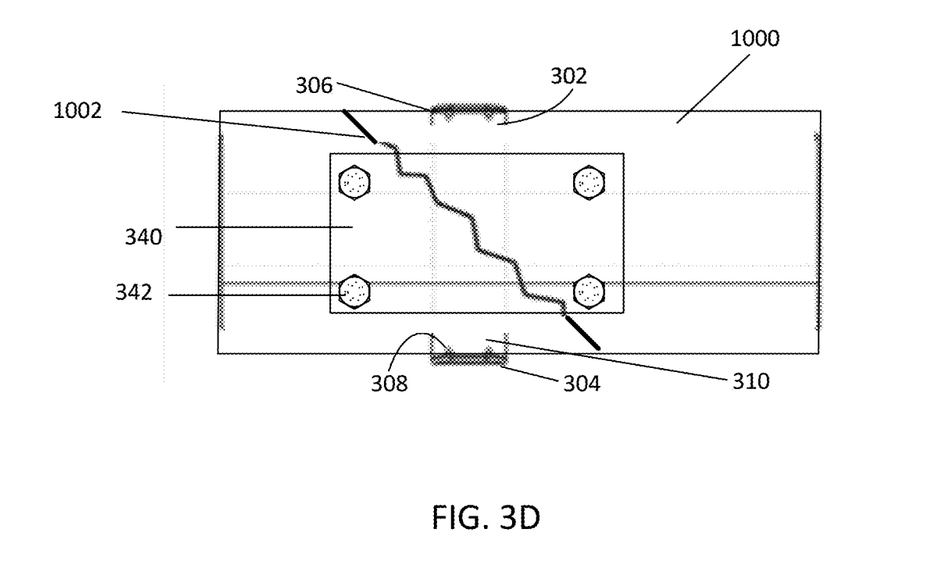
FIG. 3D shows the compression and fixation device of FIGS. 3A and 3B in a compressed state attached to a bone along with a bone plate attached to the bone.
Figure 3E:
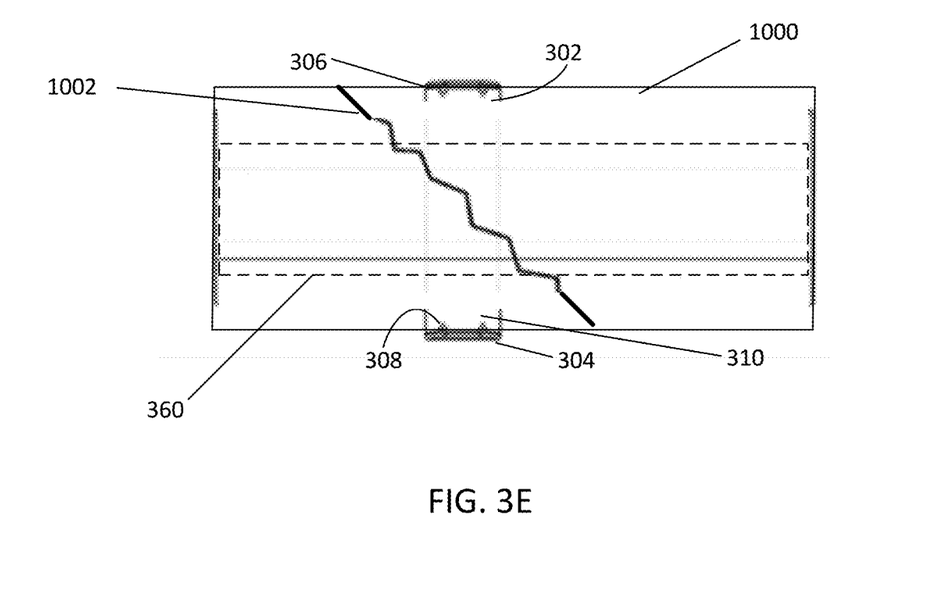
FIG. 3E shows the compression and fixation device of FIGS. 3A and 3B in a compressed state attached to a bone along with an intramedullary rod inside the bone.
Figure 4C:
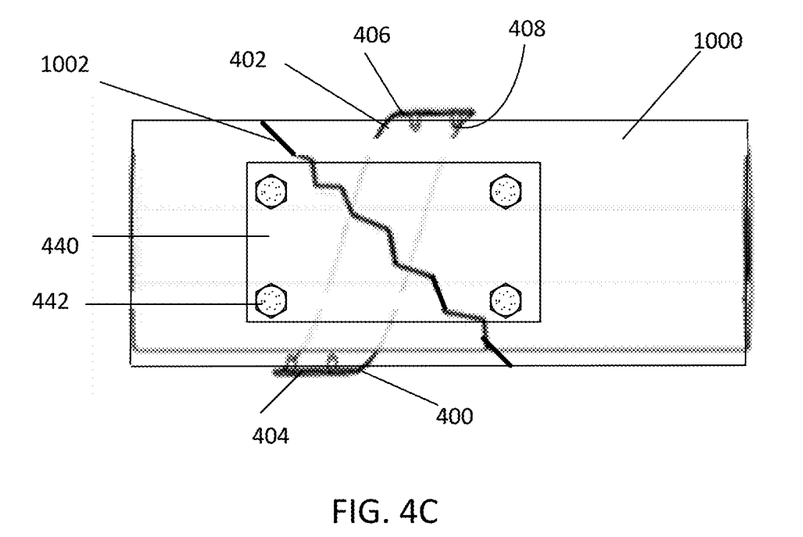
FIG. 4C shows the compression and fixation device of FIG. 4A in a compressed state attached to a bone along with a bone plate attached to the bone.
Figure 4D:
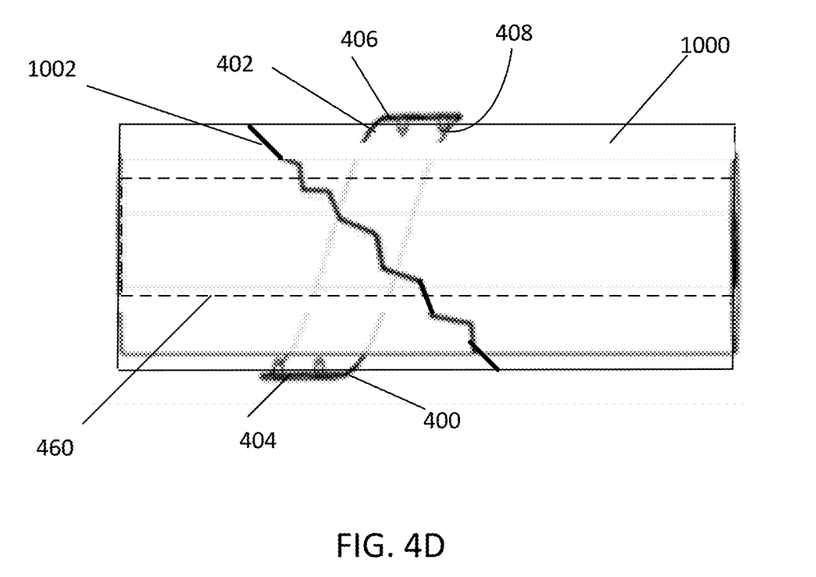
FIG. 4D shows the compression and fixation device of FIG. 4A in a compressed state attached to a bone along with an intramedullary rod inside the bone.

The compression and fixation devices 300 and 400 may be used in conjunction with bone plates. For example, as shown in FIG. 3D, the circumferential space between the ends 304 and 306 of the band 302 permit the positioning and securing of one or more bone plates 340 to the bone 1000 with fasteners 342 over the fracture plane 1002. Also, for example, as shown in FIG. 4C, the circumferential space between the ends 404 and 406 of the band 402 permit the positioning and securing of one or more bone plates 440 to the bone 1000 with fasteners 442 over the fracture plane 1002. As a result of the thin profile of the band 302, a bone plate may also be positioned over the band, and thus after the band. Moreover, a band may be structured for placement over a plate, and can facilitate placement and stability of a plate during implantation; in such procedure the band is placed after placement of the plate. Also, as shown in FIGS. 3E and 4D, the compression and fixation devices 300 and 400 may be used in conjunction with intramedullary rods 360 and 460, respectively, which are positioned within the medullary canal of the bone, across the fracture plane and prior to placement of the band.

Figure 5:
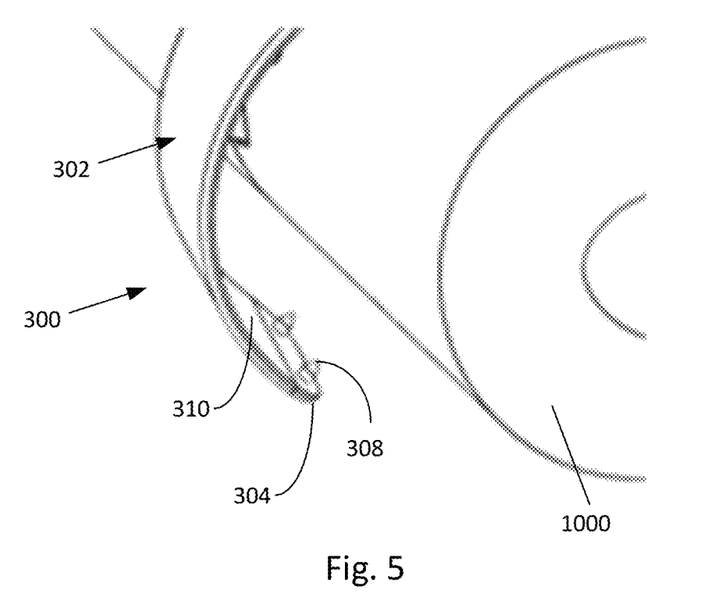
FIG. 5 shows opposing teeth on the inside surface at each end of the device of FIGS. 3A to 3C.

FIG. 5 shows details of the bone engagement structure 308 of the device 300. The bone engagement structures 308 are sturdy and sharp enough to dig into the outer cortex of the bone 1000 and anchor themselves therein when the band 302 is compressed against the bone 1000. The teeth 308 may have various shapes at their bases and have a sharp tip at the free end of the teeth. For example, the bone engagement structures 308 may have a cylindrical base extending to a conical tip or may have a pyramidal base extending to a pointed pyramid tip. The bone engagement structures 308 are sturdy so that they remain intact and undeformed even after being anchored into the bone 1000. When band 302 is compressed over the bone 1000, the bone engagement structures 308 dig in and anchor themselves into the outer cortex of the bone, thereby inhibiting the device 300 from slipping or moving relative to the bone 1000, which could alter the compressive force that is applied orthogonally to the fracture plane 1002.

Figure 6:
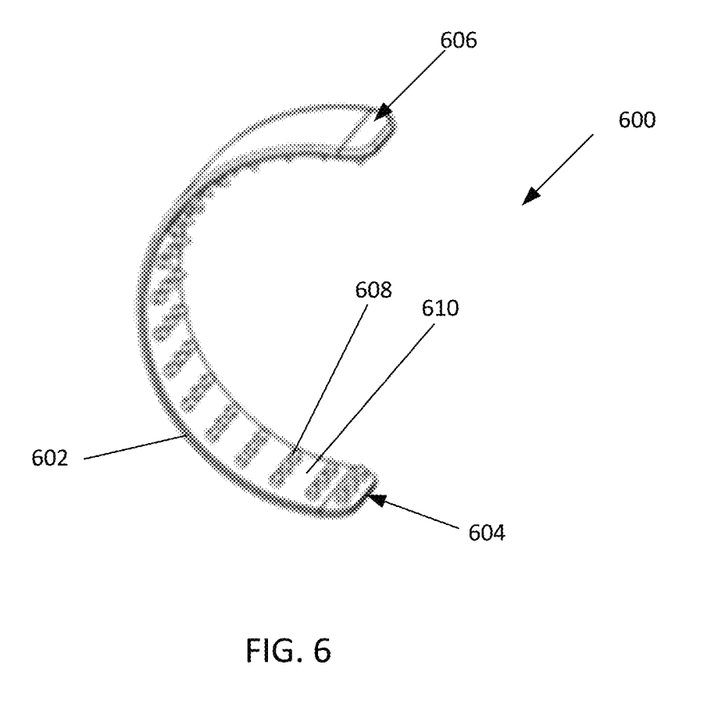
FIG. 6 shows another embodiment of a compression and fixation device, in an uncompressed state, with an increased number of teeth covering a larger surface area as compared to the embodiment shown in FIG. 5.

The number and location of the bone engagement structures 308, 408 is not limited to the ends of the bands 302, 402 of the devices 300, 400. Indeed, the number and location of the bone engagement structures 308, 408 may cover a greater surface area of the inner surface 310, 410 of the respective bands 302, 402. Such an increase in the number of the bone engagement structures can increases the potential number of anchor points between the respective bands and the bone 1000. This may be especially helpful when the device is positioned against a bone that has an irregular cross section, such as the irregular cross-sectional shape of the humerus shown in FIG. 7, and the irregular cross-sectional shapes of the tibia and fibula shown in FIGS. 8A and 8B. FIG. 6 shows an embodiment of a device 600 that includes a band 602 and a plurality of rows of bone engagement structures 608. The bone engagement structures 608 extend orthogonally from an inner surface 610 of the band 602. The rows of bone engagement structures 608 are spaced circumferentially from one another at locations between the ends 604, 606 of the band 602. Owing to the plurality of rows of bone engagement structures 608, even if some rows do not engage the bone, at least some of the bone engagement structures 608 on either side of the bone fracture plane 1002 are expected to anchor into the bone.

Figures 9A, 9B:
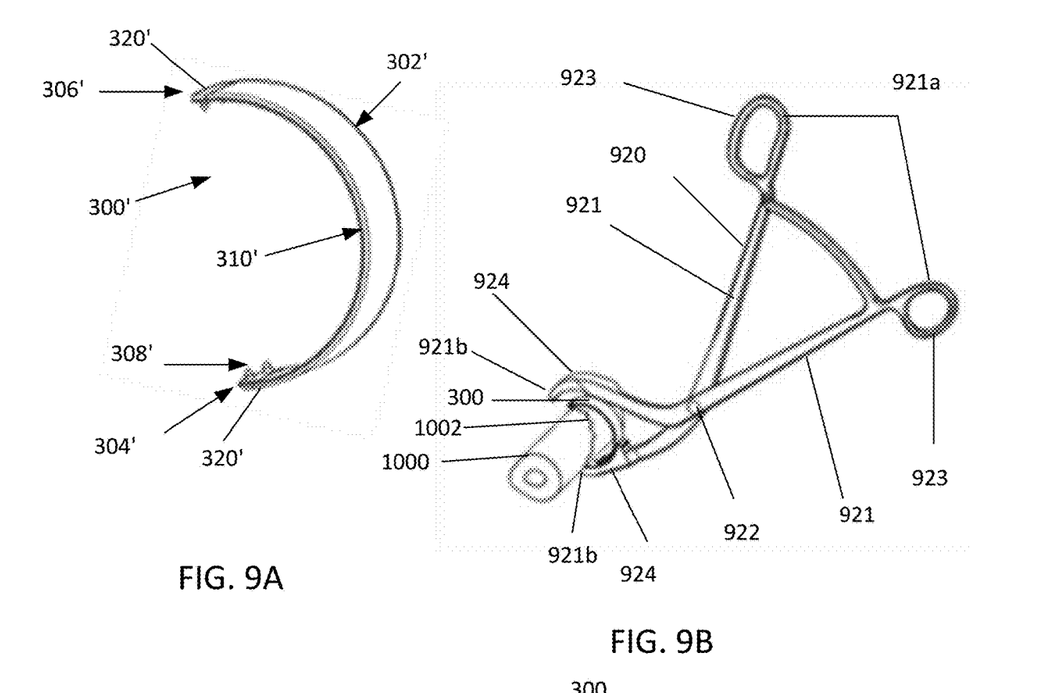
FIG. 9A shows the compression and fixation device of FIGS. 3A and 3B with a circular cross section prior to compression.
FIG. 9B shows an applier tool loaded with the uncompressed compression and fixation device of FIGS. 3A and 3B, with the compression and fixation device positioned over the fracture prior to compression.
Figure 9C:
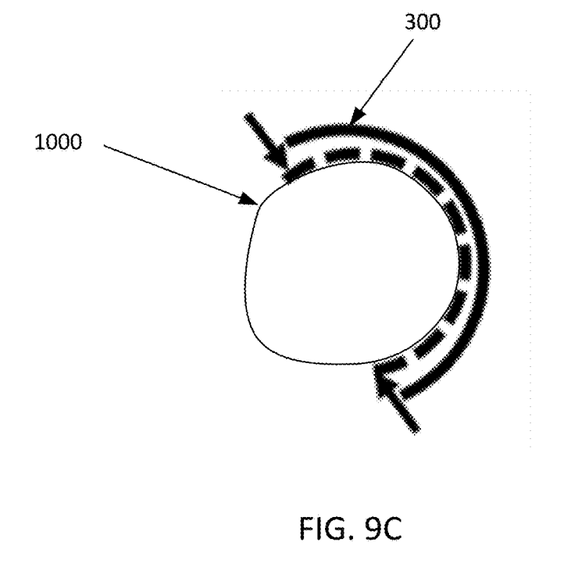
FIG. 9C shows that as a compressive force is applied to the device of FIG. 9A using the tool of FIG. 9B, the compression and fixation device conforms to the cross section of the bone.

A compression and fixation device (e.g., 300, 400, 600) may be applied manually, or with a specifically configured applier tool. FIG. 9A shows a selected compression and fixation device 300', which is an alternate embodiment of the compression and fixation device 300. In FIG. 9A, elements of compression and fixation device 300' that correspond to those of compression and fixation device 300 are shown appended with a ('). The compression and fixation device 300' differs from compression and fixation device 300 in the addition of holes 320' (shown in greater detail in FIG. 10) formed in the band 302' at the ends 304' and 306' thereof. The uncompressed compression and fixation device 300' can be loaded into an applier tool 920 (FIG. 9B). The applier tool 920 can then be used to position the uncompressed compression and fixation device 300 against the bone 1000 across the fracture plane 1002 and then to compress or "crimp" the compression and fixation device 300 around the bone 1000, as shown in FIG. 9C.

The applier tool 920 in FIG. 9B may be arranged like a surgical forceps in that it has two pivoting lever arms 921 joined and crossing at a fulcrum 922. Each arm 921 extends from proximal end 921a to a distal end 921b. Each lever 921 has a handle 923 at the proximal end 921a, and a jaw 924 at the distal end 921b. Moving the handles 923 towards one another rotates the jaws 924 towards one another in a clamping motion.

Figure 10:
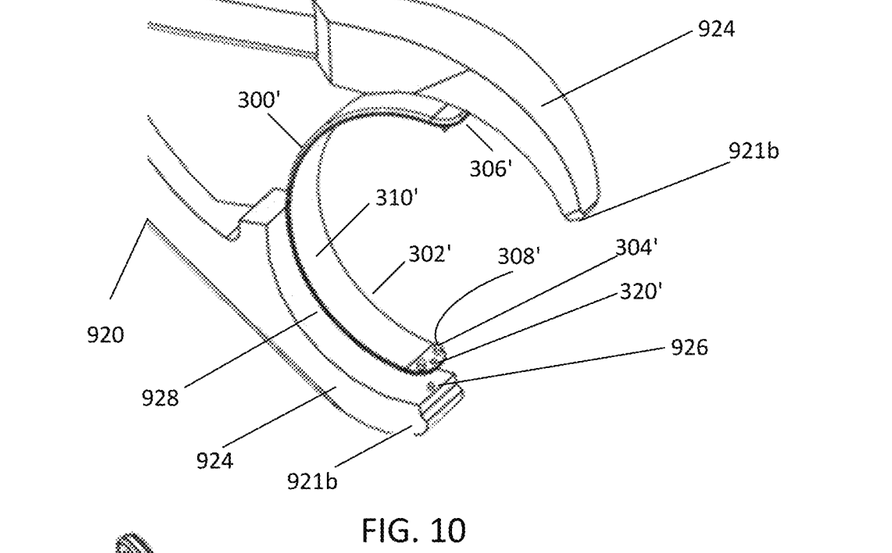
FIG. 10 shows a retaining pin or snap feature to hold another embodiment of a compression and fixation device in the crimping jaws of an applier tool during deployment.

FIG. 10 shows an exploded view of a portion of the applier tool 920 shown in FIG. 9B loaded with the compression and fixation device 300'. Each jaw 924 may have one or more retention features such as a pin, a tooth, a ridge, a blade, and the like, to engage with a corresponding or mating retention feature of the band 302' in order to retain the compression and fixation apparatus 300' between the jaws 924 while the user manipulates the applier tool 920 and positions the compression and fixation device 300' against the bone 1000. The retention features can be disengaged after the user uses the applier tool 920 to compress the compression and fixation device 300' onto the bone 1000.

For example, as shown in FIG. 10, a pin 926 protrudes from one jaw 924 toward an interior spaced between the jaws 924. The pin 926 is configured to be received into the hole 320' formed in the band 302' to retain the device 300' to the tool 920 between the jaws 924 in the uncompressed state of the device 300'. In embodiments, the protrusion 924, when received in the hole 320', does not protrude radially beyond the inner surface 310' of the band 302'. This can prevent the protrusions 924 from digging into the bone 1000 when the jaws 924 are compressed around the bone 1000.

While the compression and fixation device 300' has one hole 320' at or near at least one of the ends 304' and 306', there may be additional or alternative holes or other retention features present either at or near the ends 304' and 306' or at intermediate points between the ends 304' and 306'. Likewise, the jaws 924 may have additional or alternative corresponding retention features to engage with such additional or alternative retention features of the compression and fixation device 300'.

Each jaw 924 has a side profile that is tapered towards the distal end 921b to facilitate positioning the jaws 924 between tissue and adjacent bone, such as when the jaws 924 move into position against the bone and when the jaws 924 are moving during compression of the compression and fixation device 300'. An inner surface 928 of each jaw 924 has a curved shape that generally matches to the curvature of the compression and fixation device 300' in its pre-bent and uncompressed configuration.

Figure 11:
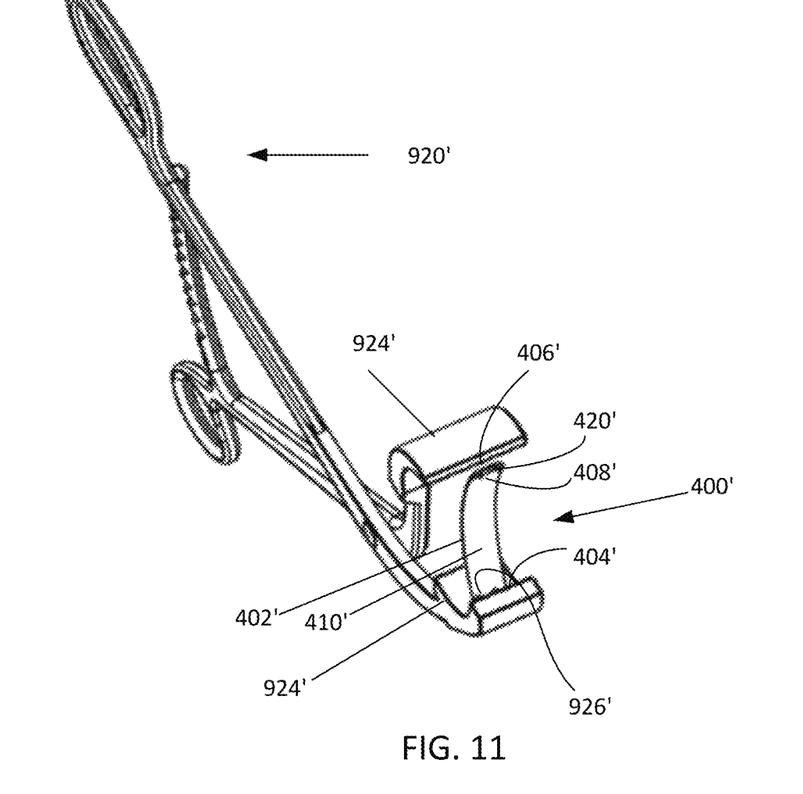
FIG. 11 shows another embodiment of jaws of an applier tool holding another embodiment of a compression and fixation device.

One alternative embodiment of an applier tool is shown in FIG. 11. In FIG. 11, elements of a tool 920' corresponding to tool 920 are shown appended with ('). The tool 920' has jaws 924' that are wider than the jaws 924 of tool 920 to accommodate offset ends 404' and 406' of a helical compression and fixation device 400', which has features corresponding to compression and fixation device 400, which are shown in FIG. 11 appended with ('). The device 400' defines one or more holes 420' in the band 402' that receive one or more protrusions 926' on one or both of the jaws 924' to retain the device 400' in the jaws 924'. The applier tool 920' has relatively wider jaws 924' than the applier tool 924 to accommodate wider compression and fixation devices, such as helical compression and fixation device 400', which is wider than non-helical compression and fixation device 300'.

The compression and fixation devices (e.g., 300, 400, 600, 300', 400') described herein are selected to fit the size and shape of the fractured bone. To facilitate selection of a suitable size and shape of a compression and fixation device, a user may use trial compression and fixation devices 1200 (FIG. 12) that are modelled on corresponding implantable compression and fixation devices. The trial devices 1200 may be available in multiple sizes and shapes for use with multiple sizes and shapes of bones. The trial compression and fixation apparatus 1200 can be elastic, disposable, formed with or without bone engaging structures, and have different malleability than the corresponding implantable implant. Also, the trial compression and fixation apparatus does not require an applier tool, such as tool 920, though a handle 1210 may be provided to manipulate and position the trial compression and fixation device 1200 against the bone at the fracture to check the size and shape of the trial compression and fixation device against the fractured bone 1000. The handle 1210 may be integrally formed with the trial compression and fixation device 1200 or may be interchangeable between a plurality of trial compression and fixation devices. The kit may also be provided with one or more plate-like implants (e.g., 340, 440) adapted to be secured onto the bone (e.g., with fasteners 342, 442), over the fracture plane 1002, and between the ends (e.g., 304, 306; 404, 406) of a compression and fixation device (e.g., 300, 400).

Figure 13:
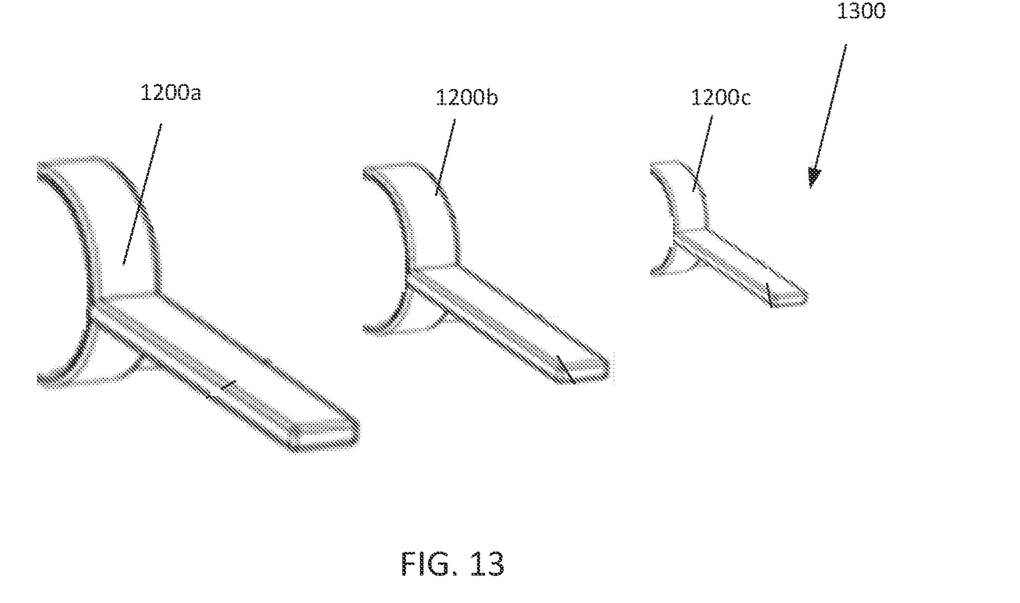
FIG. 13 shows a kit including a plurality of different trial compression and fixation devices.

In embodiments, various kits may be provided to a user, which may include any of trial compression and fixation devices, implantable compression and fixation devices, and applier tools. By way of example, one kit 1300 (FIG. 13) may include a plurality of differently sized and/or shaped trial compression and fixation devices 1200a, 1200b, 1200c are supplied as a trial kit, from which a user can select one or more of the trial devices 1200a, 1200b, 1200c for use in identifying a suitable trial compression and fixation device that matches the outer peripheral surface of the bone about the fracture plane. The kit 1300 may be supplied either with or without one or more actual, implantable, compression and fixation devices of different sizes (e.g., different widths and/or diameters), a handle, or an applier tool.

The compression and fixation devices (e.g., 300, 400, 600, 300', 400') described herein may be used in accordance with the following exemplary workflow. In the example workflow, reference will be made to the compression and fixation device 300' and the applier tool 920, although it will be appreciated that the workflow is applicable to all of the embodiments of compression and fixation devices described herein. Moreover, it will be appreciated that the compression and fixation devices described herein may be used and compressed onto bone by hand without an applier tool.

Figure 12:
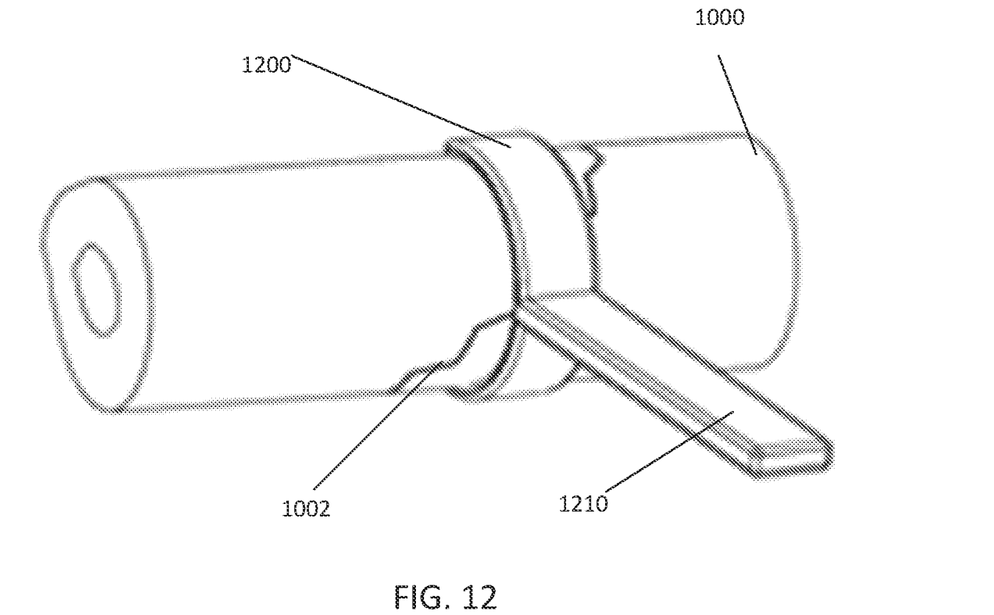
FIG. 12 shows an embodiment of a trial compression and fixation device applied to a fractured bone.

To check the approximate fit between a respective fractured bone (e.g., 1000) and an implantable compression and fixation device 300', a user may select one trial device 1200 at a time and apply the selected trial device to the bone 1000 without compressing the trial device 1200 so that the trial device 1200 straddles the fracture plane 1002 and curves circumferentially around the bone at least 180°, as shown in FIG. 12. The trial device 1200 is applied at the intended location of the corresponding implantable compression and fixation device 300', i.e., across the fracture plane 1002. Specifically, the trial device 1200 is applied so that it straddles the fracture plane (e.g., 1002) and is applied from the side of the bone 1000 from which the fracture will be approached for fixation of the compression and fixation device 300'.

When a user selects a trial device 1200 that most closely matches the size and shape of the bone 1000 at the intended location of the implanted compression and fixation device 300', the user selects the compression and fixation device 300' corresponding to the selected trial device 1200 for compression over the bone fracture plane 1002.

The user can then load the compression and fixation device 300' into the jaws 924 of the applier tool 920, by inserting the pin 926 into the hole 320' in the band 302 so that the compression and fixation device 300' is retained between the jaws 924. Once the device 300' is loaded and retained in the jaws 924, the user grasps the handles 923 and manipulates the jaws 924 and the device 300' between bone and adjacent tissue to position the device 300' against the bone so that the device 300' straddles the fracture plane 1002. Then, a user squeezes the handles 923 towards each other to cause the jaws 924 to pivot about the fulcrum 922 to compress the device 300' onto the bone 1000. Once the device 300' is compressed and the bone engagement structures 308' are anchored into the bone 1000, the user opens the jaws 924 by moving the handles 923 apart from one another, which releases the pin 926 out of the hole 320' so that the user can withdraw the tool 920 away from the fracture bone.

The compression and fixation devices and methods described herein provide many benefits. The compression and fixation devices may be used to reduce a fracture in conjunction with internal devices such as intramedullary rods and external bone plates. The compression and fixation devices have relatively thin profiles (e.g, less than 2 mm thick), reducing the trauma caused by the devices to surrounding tissue. Additionally, the compression and fixation devices described herein do not require the formation of holes through bone, which are required for using a lag screw. Indeed, the use of the compression and fixation devices in accordance with this disclosure eliminates the conventional clamping, measuring, and drilling of bone and use of lag screws, thereby saving time and potentially reducing complications. Moreover, the compression and fixation devices may be used for temporary fixation to the bone, or may be left in the patient as a permanent implant. Also, by providing compression and fixation devices in various sizes and shapes, a compression and fixation device can be found that is compatible with almost any bone fracture.

There have been described and illustrated herein several embodiments of a bone fracture reduction apparatus, system, and a method of use. While particular embodiments of the invention have been described, it is not intended that the invention be limited thereto, as it is intended that the invention be as broad in scope as the art will allow and that the specification be read likewise. Thus, while particular materials used for the compression and fixation devices have been disclosed, it will be appreciated that other suitable materials may be used as well. In addition, while particular types of applier tools have been disclosed, it will be understood that other applier tools may be used or the compression and fixation device may be compressed manually by the user without a specific tool. It will therefore be appreciated by those skilled in the art that yet other modifications could be made to the provided invention without deviating from its spirit and scope as claimed.

What is claimed is:

1. An extramedullary compression and fixation apparatus consisting of:
   a pre-curved, malleable band having a first free end and a second free end, the pre-curved, malleable band extending along a portion of a helix such that the first and second free ends are circumferentially spaced by at least 180 degrees about a central longitudinal axis of the helix and the first and second free ends are longitudinally offset about the central longitudinal axis; and
   at least one bone engaging structure protruding from the pre-curved, malleable band toward an interior space defined by the pre-curved, malleable band,
   the pre-curved, malleable band configured to be compressed over a bone fracture site of a bone into permanent deformation of the pre-curved, malleable band to conform the curvature of the pre-curved, malleable band to a curvature of a surface of the bone around the bone fracture site, the at least one bone engaging structure configured to dig into an outer cortex of the bone when the pre-curved, malleable band is compressed over the bone fracture site, and wherein the pre-curved, malleable band is configured to maintain compression of the bone across the bone fracture site upon being compressed without external fixation devices,
the pre-curved, malleable band including no holes specifically adapted for receiving screws.

2. The apparatus according to claim 1, wherein:
the pre-curved, malleable band extends in a semicircle.

3. The apparatus according to claim 1, wherein:
at least one of the at least one bone engaging structure is located at or near the first end and at least one of the at least one bone engaging structure is located at or near the second end.

4. The apparatus according to claim 1, wherein:
the at least one bone engaging structure extends from an inner surface of the band.

5. The apparatus according to claim 1, wherein:
the first free end and the second free end of the pre-curved, malleable band are configured for receiving retention features of an applier tool configured to position the pre-curved, malleable band against the bone and to compress the pre-curved, malleable band onto the bone.

6. The apparatus according to claim 5, wherein:
the pre-curved, malleable band defines at least one hole or socket at the free first end and at least one hole or socket at the second free end, wherein the holes or sockets are configured to receive corresponding protrusions of the applier tool to couple the pre-curved, malleable band to the applier tool.

7. A fracture reduction kit, comprising:
an extramedullary compression and fixation apparatus consisting of:
 a pre-curved, malleable band having a first free end and a second free end, pre-curved, malleable band extending along a portion of a helix such that the first and second free ends are circumferentially spaced by at least 180 degrees about a central longitudinal axis of the helix and the first and second free ends are longitudinally offset about the central longitudinal axis; and
 at least one bone engaging structure protruding from the pre-curved, malleable band toward an interior space defined by the pre-curved, malleable band,
 the pre-curved, malleable band configured to be compressed over a bone fracture site of a bone into permanent deformation of the pre-curved, malleable band to conform the curvature of the pre-curved, malleable band to a curvature of a surface of the bone around the bone fracture site, the at least one bone engaging structure configured to dig into an outer cortex of the bone when the pre-curved, malleable band is compressed over the bone fracture site, and wherein the pre-curved, malleable band is configured to maintain compression of the bone across the bone fracture site upon being compressed without external fixation devices; and
a compression tool operable to apply a sufficient force to the first and second free ends of the compression and fixation apparatus to compress the pre-curved, malleable band about a portion of a circumference of the bone.

8. The kit according to claim 7, wherein:
the compression tool is removably coupled to the compression and fixation apparatus.

9. The kit according to claim 7, further comprising:
a trial compression and fixation apparatus that is a model of the compression and fixation apparatus, wherein the trial compression and fixation apparatus is configured for placement over the bone fractured site to determine whether the trial compression and fixation apparatus best fits the curvature of the bone fracture site.

10. The kit according to claim 7, further comprising:
at least one of an intramedullary rod configured to extend in an intramedullary canal of the fractured bone across a fracture plane of the bone fracture site, and a bone plate configured to be attached over the bone fracture site.

11. A fracture reduction system, comprising:
an extramedullary compression and fixation apparatus, consisting of,
 a pre-curved, deformable band having a first free end and a second free end, the pre-curved, deformable band extending along a portion of a helix such that the first and second free ends are circumferentially spaced by at least 180 degrees about a central longitudinal axis of the helix and the first and second ends are longitudinally offset about the central longitudinal axis; and
 at least one bone engaging structure protruding from the pre-curved, deformable band toward an interior space defined by the pre-curved, deformable band,
 the pre-curved, deformable band configured to be compressed over a bone fracture site of a bone to conform the curvature of the pre-curved, deformable band to a curvature of a surface of the bone around the bone fracture site, the at least one bone engaging structure configured to dig into an outer cortex of the bone when the pre-curved, deformable band is compressed over the bone fracture site, and wherein the pre-curved, deformable band is configured to maintain compression of the bone across the bone fracture site upon being compressed without external fixation devices; and
an applier tool operable to apply a sufficient force to the first and second free ends of the compression and fixation apparatus to compress the pre-curved, deformable band about the bone across the bone fracture site.

12. The system according to claim 11, wherein:
the applier tool is configured to receive and retain the compression and fixation apparatus in an uncompressed state prior to being crimped.

13. A method of bone fracture reduction comprising:
a) applying one or more trial compression and fixation apparatus to an exterior of a fractured bone so that the trial compression and fixation apparatus extends across a fracture plane to determine which one trial compression and fixation apparatus is a best fit for the fractured bone across the fracture plane;
b) selecting an implantable extramedullary compression and fixation apparatus corresponding to the trial compression and fixation apparatus determined to be the best fit, the extramedullary compression and fixation apparatus having a first free end and a second free end, the pre-curved, deformable band extending along a portion of a helix such that the first and second free ends are circumferentially spaced by at least 180 degrees about a central longitudinal axis of the helix and the first and second free ends are longitudinally offset about the central longitudinal axis; and c) compressing the selected implantable extramedullary compression and fixation apparatus into permanent deformation onto the bone over and across the fracture plane.

14. The method according to claim 13, wherein:
the compressing of the selected implantable extramedullary compression and fixation apparatus onto the bone causes the at least one bone engaging structure to dig into the cortex of the bone.

15. The method according to claim 13, further comprising:
implanting an intramedullary apparatus within the fractured bone across the fracture plane prior to compressing the selected implantable extramedullary compression and fixation apparatus onto the bone over and across the fracture plane.

16. The method according to claim 13, further comprising:
implanting a cortical bone plate on the fractured bone across the fracture plane.

\* \* \* \* \*